United States Patent
Dye et al.

(10) Patent No.: US 8,046,909 B2
(45) Date of Patent: Nov. 1, 2011

(54) METHOD OF FABRICATING STIMULATION LEAD

(75) Inventors: Don Dye, Plano, TX (US); Kevin Turner, Frisco, TX (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 0 days.

(21) Appl. No.: 12/766,356

(22) Filed: Apr. 23, 2010

(65) Prior Publication Data

US 2010/0269339 A1 Oct. 28, 2010

Related U.S. Application Data

(60) Provisional application No. 61/172,424, filed on Apr. 24, 2009.

(51) Int. Cl.
*H01R 43/00* (2006.01)
(52) U.S. Cl. .............. 29/825; 29/868; 29/869; 607/116; 607/122
(58) Field of Classification Search .................... 29/825, 29/868, 869; 607/116, 122
See application file for complete search history.

(56) References Cited

U.S. PATENT DOCUMENTS

| 7,108,549 | B2 * | 9/2006 | Lyu et al. ...................... 439/587 |
| 7,395,116 | B2 * | 7/2008 | Mehdizadeh et al. .......... 607/37 |
| 7,740,780 | B2 * | 6/2010 | Hamboly .................. 264/171.12 |
| 7,877,869 | B2 * | 2/2011 | Mehdizadeh et al. .......... 29/842 |
| 2006/0173262 | A1 | 8/2006 | Hegland et al. |
| 2010/0077606 | A1 | 4/2010 | Black et al. |

* cited by examiner

*Primary Examiner* — Carl Arbes
(74) *Attorney, Agent, or Firm* — Craig Hoersten; Christopher S. L. Crawford; Melissa Acosta (57) ABSTRACT

In one embodiment, a process, for fabricating a medical lead comprises: providing a splicing tube having a plurality of angularly spaced longitudinal grooves; placing a first plurality of conductors within the plurality of angularly spaced grooves defined on an exterior surface of the splicing tube; placing a second plurality of conductors within the plurality of angularly spaced grooves and adjacent to the first plurality of conductors such that a portion of the distal ends overlap a portion of the proximal ends; positioning conductive filler material adjacent to the overlapped portions of the distal and proximal ends; electrically coupling the proximal ends of the first plurality of electrodes to respective proximal ends of the second plurality of electrodes; molding insulative material about at least the electrode assembly and the splicing tube; and fusing the splicing tube with the insulative material from the molding and the lead body.

19 Claims, 12 Drawing Sheets

METHOD OF FABRICATING STIMULATION LEAD

CROSS-REFERENCE TO RELATED APPLICATIONS

This application claims the benefit of U.S. Provisional Application No. 61/172,424, filed Apr. 24, 2009, which is incorporated herein by reference.

TECHNICAL FIELD

This application relates in general to medical leads, and in particular to medical leads with segmented electrodes and methods of fabrication.

BACKGROUND INFORMATION

Deep brain stimulation (DBS) refers to the delivery of electrical pulses into one or several specific sites within the brain of a patient to treat various neurological disorders. For example, deep brain stimulation has been proposed as a clinical technique for treatment of chronic pain, essential tremor, Parkinson's disease (PD), dystonia, epilepsy, depression, obsessive-compulsive disorder, and other disorders.

A deep brain stimulation procedure typically involves first obtaining preoperative images of the patient's brain (e.g., using computer tomography (CT) or magnetic resonance imaging (MRI)). Using the preoperative images, the neurosurgeon can select a target region within the brain, an entry point on the patient's skull, and a desired trajectory between the entry point and the target region. In the operating room, the patient is immobilized and the patient's actual physical position is registered with a computer-controlled navigation system. The physician marks the entry point on the patient's skull and drills a burr hole at that location. Stereotactic instrumentation and trajectory guide devices are employed to control of the trajectory and positioning of a lead during the surgical procedure in coordination with the navigation system.

Brain anatomy typically requires precise targeting of tissue for stimulation by deep brain stimulation systems. For example, deep brain stimulation for Parkinson's disease commonly targets tissue within or close to the subthalamic nucleus (STN). The STN is a relatively small structure with diverse functions. Stimulation of undesired portions of the STN or immediately surrounding tissue can result in undesired side effects. Mood and behavior dysregulation and other psychiatric effects have been reported from stimulation of the STN in Parkinson's patients.

To avoid undesired side effects in deep brain stimulation, neurologists often attempt to identify a particular electrode for stimulation that only stimulates the neural tissue associated with the symptoms of the underlying disorder while avoiding use of electrodes that stimulate other tissue. Also, neurologists may attempt to control the pulse amplitude, pulse width, and pulse frequency to limit the stimulation field to the desired tissue while avoiding other tissue.

As an improvement over conventional deep brain stimulation leads, leads with segmented electrodes have been proposed. Conventional deep brain stimulation leads include electrodes that fully circumscribe the lead body. Leads with segmented electrodes include electrodes on the lead body that only span a limited angular range of the lead body. The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. For example, at a given position longitudinally along the lead body, three electrodes can be provided with each electrode covering respective segments of less than 120° about the outer diameter of the lead body. By selecting between such electrodes, the electrical field generated by stimulation pulses can be more precisely controlled and, hence, stimulation of undesired tissue can be more easily avoided.

Implementation of segmented electrodes are difficult due to the size of deep brain stimulation leads. Specifically, the outer diameter of deep brain stimulation leads can be approximately 0.05 inches or less. Fabricating electrodes to occupy a fraction of the outside diameter of the lead body and securing the electrodes to the lead body can be quite challenging.

SUMMARY

In one embodiment, a process, for fabricating a medical lead for stimulation of tissue of a patient, comprises: providing an electrode assembly comprising a plurality of electrodes electrically coupled to a first plurality of conductors; providing a lead body comprising a second plurality of conductors; providing a splicing tube having a plurality of angularly spaced longitudinal grooves; placing proximal ends of the first plurality of conductors within the plurality of angularly spaced grooves defined on an exterior surface of the splicing tube; placing distal ends of the second plurality of conductors within the plurality of angularly spaced grooves and adjacent to the proximal ends of the first plurality of conductors such that a portion of the distal ends overlap a portion of the proximal ends; positioning conductive filler material adjacent to the overlapped portions of the distal and proximal ends; electrically coupling the proximal ends of the first plurality of electrodes to respective proximal ends of the second plurality of electrodes; molding insulative material about at least the electrode assembly and the splicing tube; and fusing the splicing tube with the insulative material from the molding and the lead body.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

The present application is generally related to fabrication of a stimulation lead comprising segmented electrodes in an efficient and robust manner. In some embodiments, an electrode assembly is provided that enables multiple segmented electrodes to be readily coupled to wire conductors. In some embodiments, multiple electrode assemblies are successively coupled to wires in a linear manner to form an array of segmented electrode assemblies. After assembly of the array, over-molding is performed to integrate the assemblies to a lead body to form the stimulation lead.

Figure 1A:
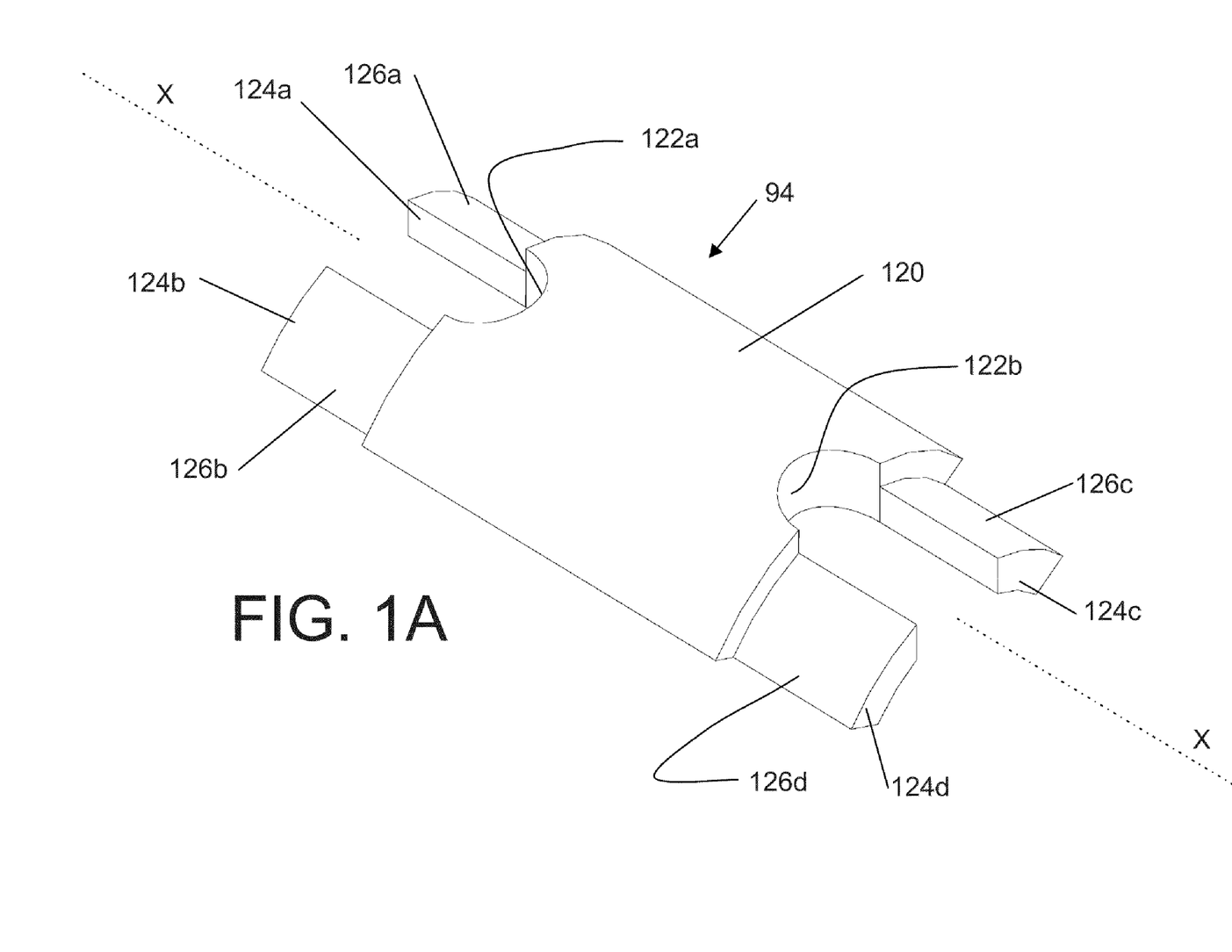
FIG. 1A is an isometric view of an inventive segmented electrode.

FIG. 1A depicts segmented electrode 94 that may be included within an electrode assembly according to one representative embodiment. Segmented electrode 94 has a convex exterior surface 120 which delivers a stimulation pulse to surrounding tissue. In some embodiments, side recesses 122a and 122b provide a flow path for polymer material during injection molding. Also, segmented electrode 94 comprises one or more projections 124a-124d extending from the sides of the segmented electrode. In the illustrated embodiment, the projections 124a-124d are longitudinal projections extending parallel to the longitudinal axis X-X. Each of the projections 124a-124d has an exterior surface 126a-126d which is at a sufficient depth below the surface 120 to allow insulative material to over mold a portion of the segmented electrode 94 to integrate the electrode 94 within the lead body. That is, projections 124a-124d engage and anchor the segmented electrode 94 to the lead body after the overmolding process is completed.

Figures 1B, 1F:
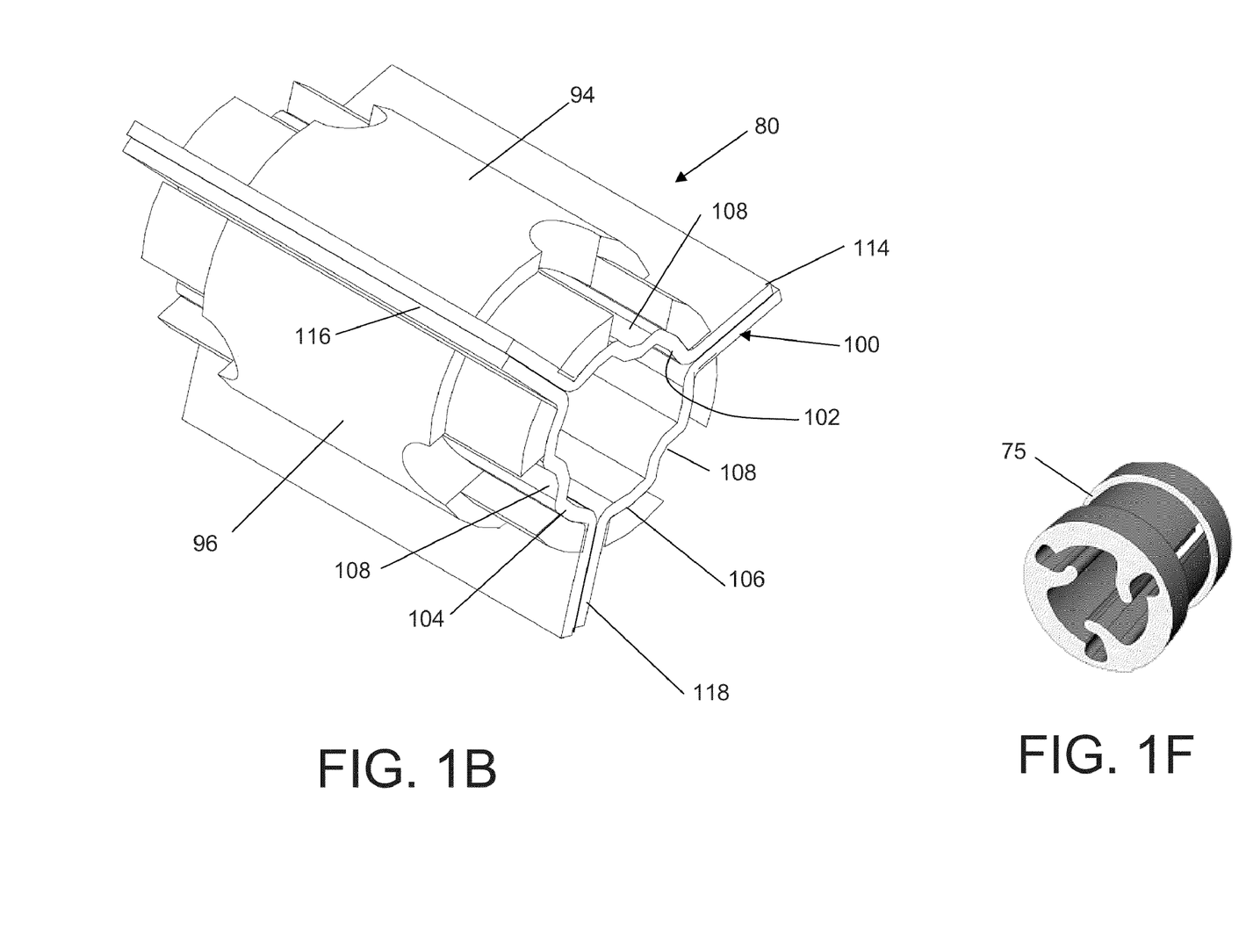
FIG. 1B is an isometric view of an inventive electrode assembly which incorporates the segmented electrode of FIG. 1A according to one representative embodiment.
FIG. 1F depicts a frame that may be utilized to fabricate segmented electrode assemblies according to one representative embodiment.

In one embodiment illustrated in FIG. 1B, multiple segmented electrodes 94, 96, and 98 (not shown in FIG. 1B) are attached to each other by backing or separator structure 100 forming electrode assembly 80. In one embodiment, structure 100 includes one or more strips of a polymer tape, such as BIONATE® tape. BIONATE® is a thermoplastic polycarbonate urethane. BIONATE® is preferred due to its widely accepted characteristics for biomedical applications, although any other suitable biocompatible, thermoplastic material could be employed. The attachment of the segmented electrodes 94, 96, and 98 to the tape provides a relatively efficient manner to initially hold segmented electrodes 94, 96, and 98 in a fixed relationship during lead fabrication.

Although three segmented electrodes are shown, any suitable number of segmented electrodes could be attached to the tape segment(s). Also, in one embodiment, structure 100 comprises three strips of tape, although a continuous single strip of tape could be used in one alternative embodiment. As shown in FIG. 1B, strip 102 structures segmented electrode 94. Strips 104 and 106 structure segmented electrodes 96 and 98, respectively. Strips 102, 104, and 106 are also attached to each other to hold segmented electrodes 94, 96, and 98 in an annular configuration.

Side portions of each strip may be folded and placed next to adjacent side portions of the adjacent strips to form ribs 114, 116, and 118. The ribs 114, 116, and 118 act as angular spacers for the segmented electrodes 94, 96, and 98, respectively. Further, in certain embodiments, each strip 102, 104, and 106 is folded to form indents 108. In an alternative embodiment, strips of tape could be employed to hold segmented electrodes together and to attach the electrodes to a frame (e.g., frame 75 as shown in FIG. 1F) of suitable biocompatible, thermoplastic material. The thermoplastic frame could comprise a conduit for passing conductors for facilitating assembly of an array of electrode assemblies. Also, the frame could comprise indents for holding conductor wires for subsequent welding. Preferably, the material of the frame would be selected to flow at the same temperature as other insulative material of the lead to permit a seamless, gapless lead body to be formed.

Figure 1C:
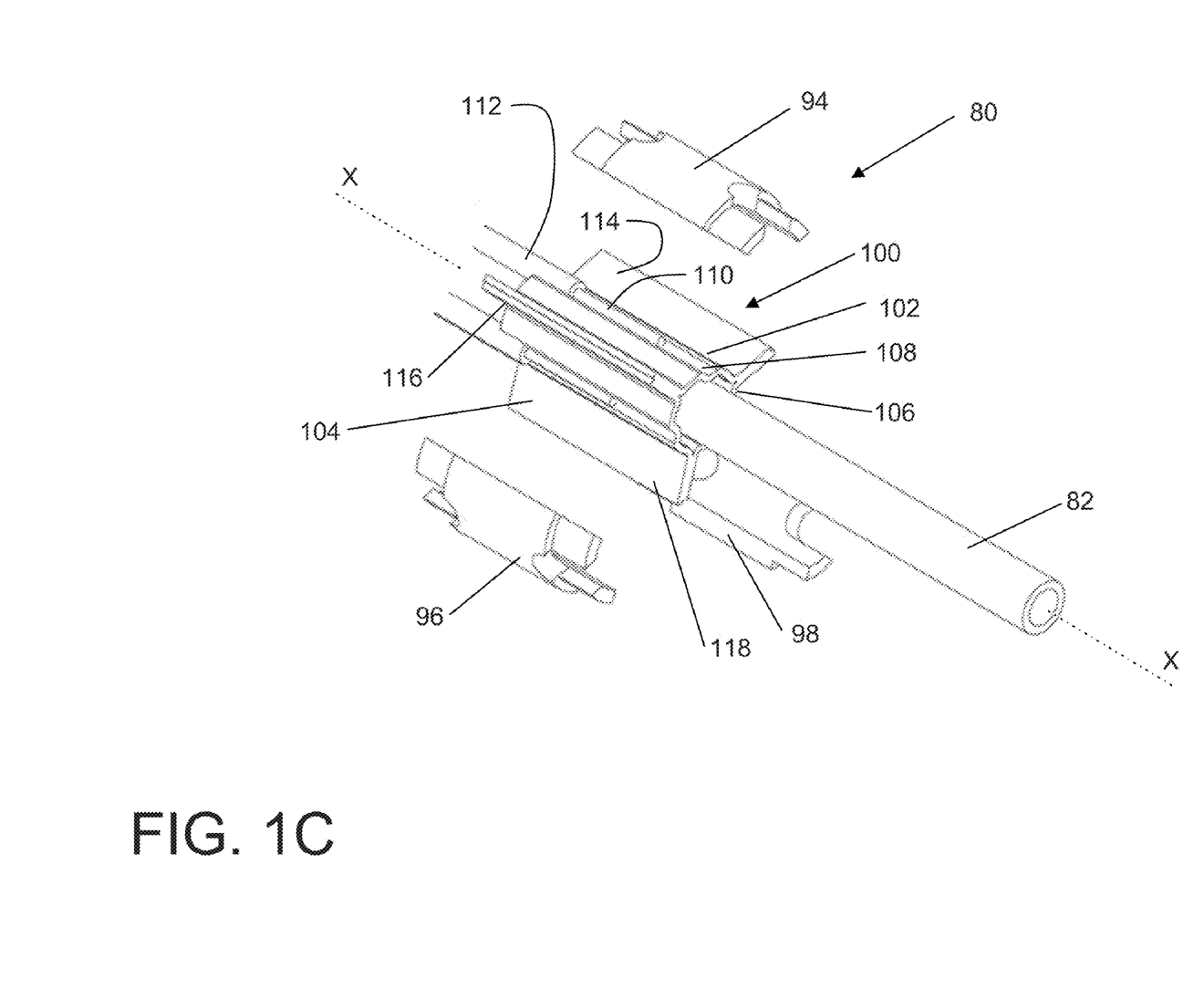
FIG. 1C is an isometric partially exploded view of an electrode assembly which incorporates the segment electrode of FIG. 1A.

Electrode assembly 80 holds segmented electrodes 94, 96, and 98 in a fixed configuration for integration with the lead body. The integration process begins by placing electrode assembly 80 over stylet tubing 82 as shown in FIG. 1C. FIG. 1C is a partially exploded isometric view to more clearly depict the assembly process. Exposed surfaces 110 of conductors 112 are preferably placed underneath electrodes 94, 96, and 98 and within indents 108. The conductors 112 are preferably obtained from the distal end of a pre-formed lead body as will be discussed in greater detail below. Exposed surfaces 110 are preferably welded to segmented electrodes 94, 96, and 98.

Although some embodiments integrate segmented electrodes into a completed assembly before integrating the assembly with other components (e.g., the stylet tubing and conductor wires) of a stimulation lead, alternative embodiments may form the assembly in a piecemeal manner about or around such other components. In such an embodiment, each individual segmented electrode is placed about center tubing with one or more segments of thermoplastic tape. As the electrodes are placed, the segments of tape for adjacent electrodes are joined to form the various ribs. Also, in some embodiments, suitable adapted tooling may be provided to hold one or more segmented electrodes while an electrode assembly is being completed.

Figure 1D:
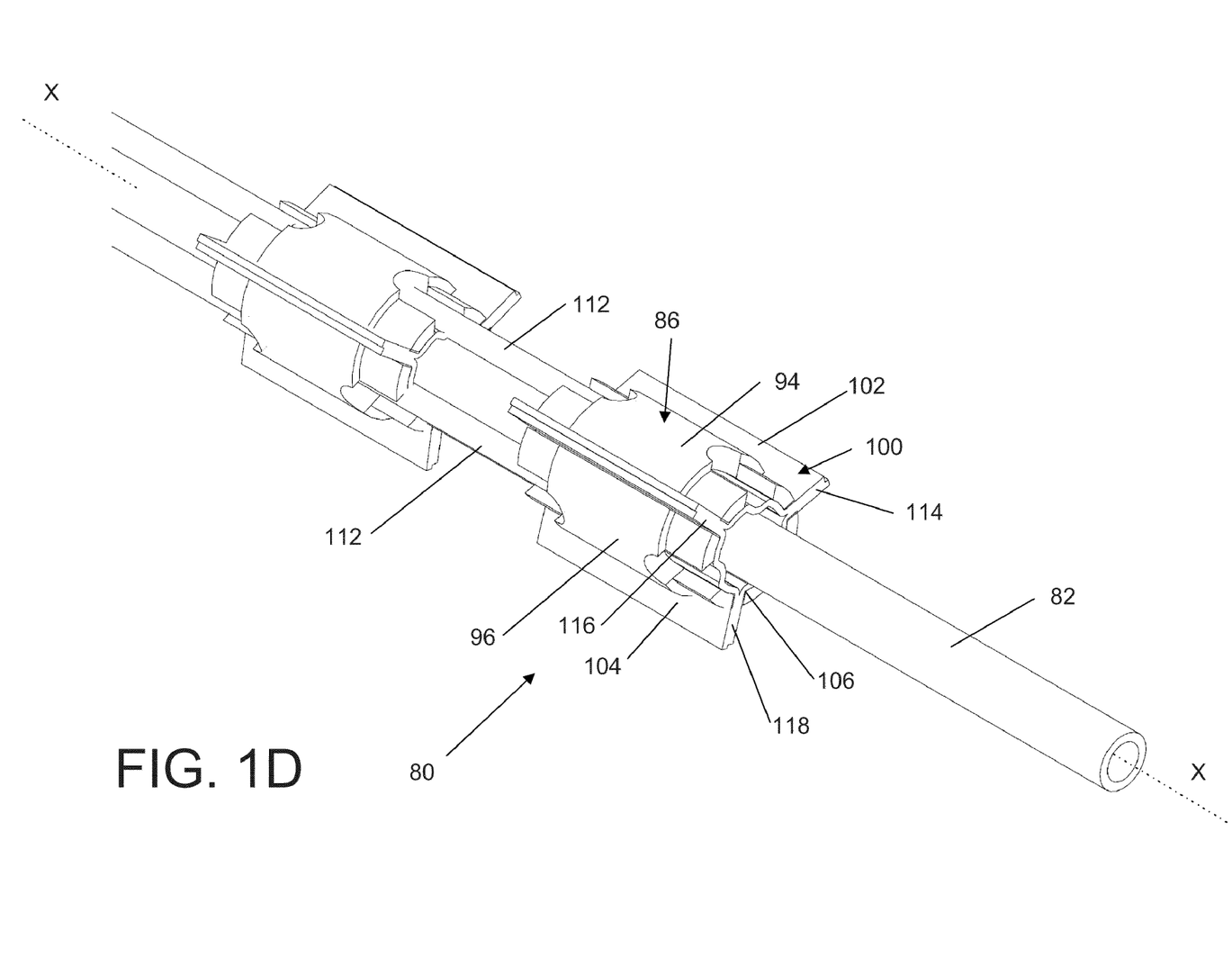
FIG. 1D is an isometric view of a distal end portion of a medical lead during a fabrication process incorporating the electrode assembly of FIG. 1B.
Figure 1E:
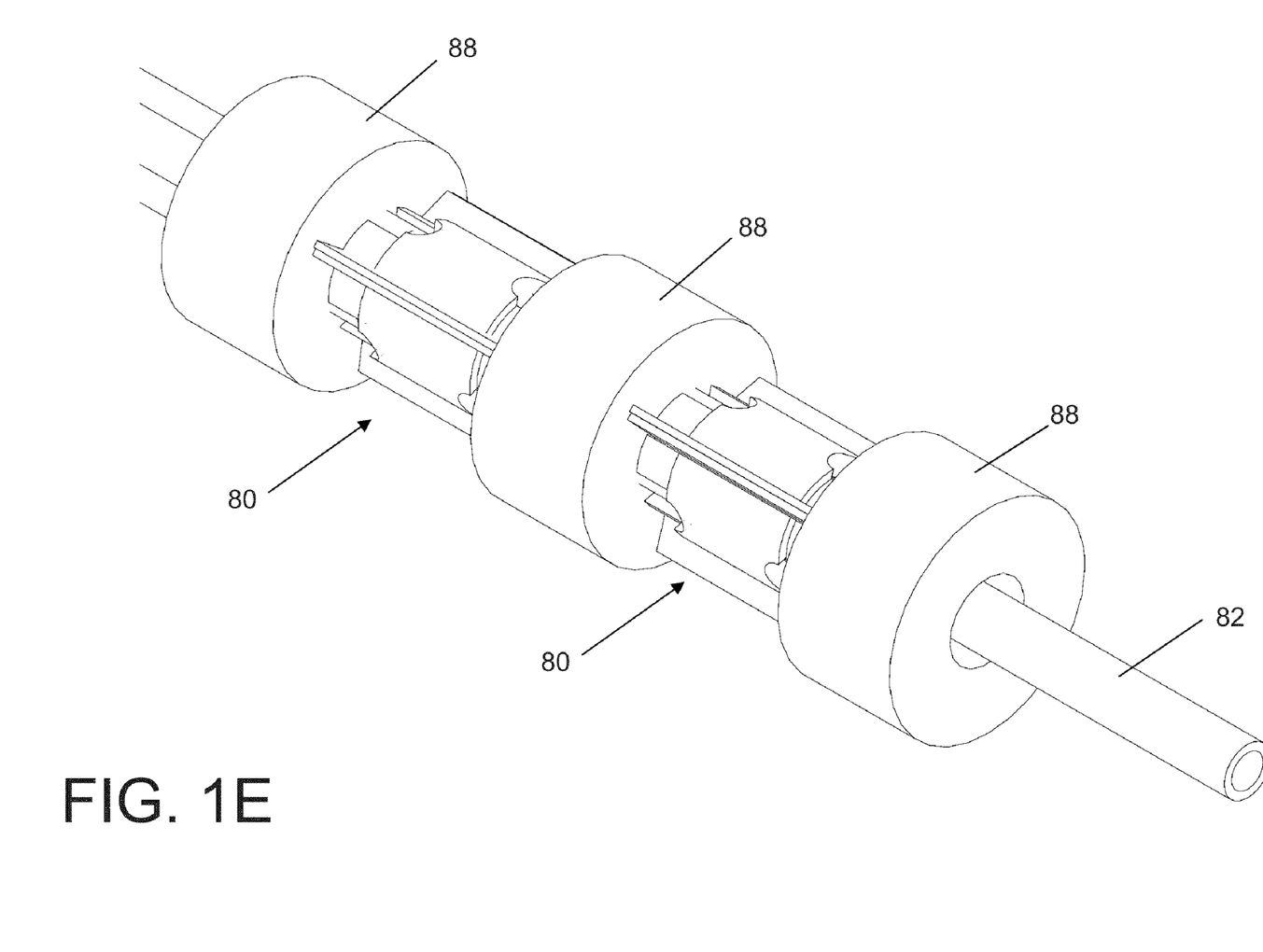
FIG. 1E is another isometric view of a distal end portion of a medical lead during a fabrication process incorporating the electrode assembly of FIG. 1B.

FIG. 1D depicts a detailed partial isometric view of multiple electrode assemblies arranged in a serial manner about tubing 82. The conductors 112 for each subsequent stage are preferably threaded between the outside surface of tubing 82 and the inner surface of the structures 100 of preceding assemblies 80. In another embodiment shown in FIG. 1E, spacers 88 are placed between adjacent electrode assemblies 80 or other lead components such as a conventional ring electrode (not shown), a conventional tip electrode (not shown), or a conventional transition sleeve (not shown). Spacers 88 are preferably fabricated from suitable thermoplastic, biocompatible material. Spacers 88 are used to maintain each electrode assembly 80 at a precise position relative to each other during the fabrication process.

Upon completion of the array of electrode assemblies 80 with the segmented electrodes coupled to conductors 112, the array is placed within a suitable mold for overmolding. In one preferred embodiment, the same material is used for spacers 88, the thermoplastic tape, and the material used for subsequent injection molding. The applied material flows around and inside the segmented electrode assemblies. Also, the heat and pressure of the overmolding places the electrode structure 100 (and spacers 88) in a state of flow which fuses with the injected material, and, at least in part, results in a filling of regions between the segmented electrodes 94, 96, and 98. Consequently, in the finished lead, the segmented electrodes 94, 96 and 98 will be partially surrounded and supported by a fused matrix of material. Also, due to the configuration of each segmented electrode (see projections 124a-124d in FIG. 1A), the segmented electrodes are mechanically integrated within the insulative material in a relatively robust manner, as opposed to being merely attached to the outside surface of the insulative material. After the overmolding is completed, centerless grinding is preferably performed to remove excess material and to create an outside diameter of uniform size.

Figure 2:
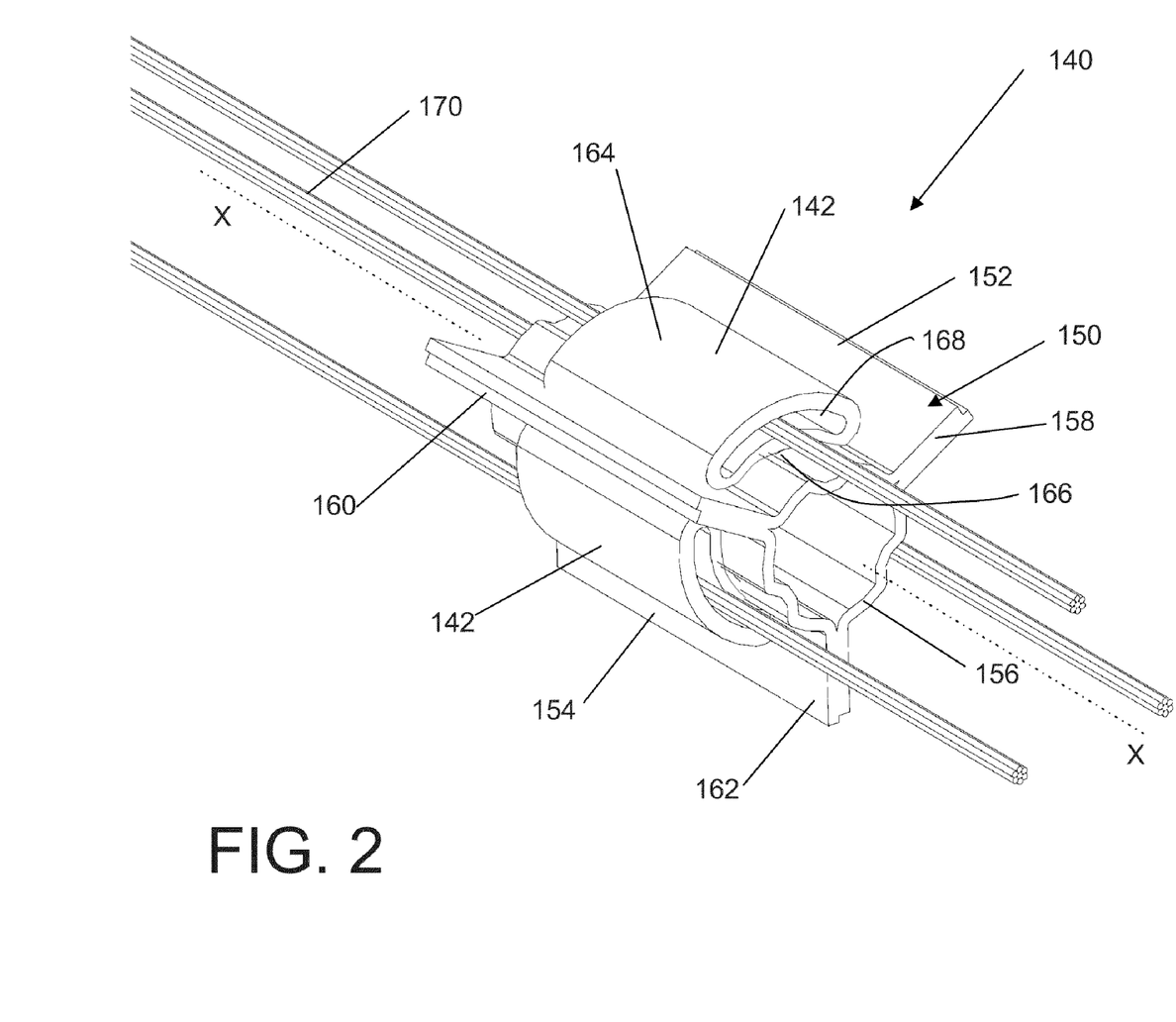
FIG. 2 is an isometric view of another inventive electrode assembly that includes a segmented electrode.

FIG. 2 illustrates another embodiment of a segmented electrode assembly 140. The segmented electrode assembly 140 is similar to the assembly 80 discussed above except that the segmented electrodes have a different shape and form of engagement with the material matrix of the final body. As shown in FIG. 2, the center tubing and the spacers are omitted for clarity. For brevity and clarity, a description of many components which are identical or similar to those described in connection with FIGS. 1A through 1E will not be repeated here. Reference should be made to the foregoing paragraphs with the following description to arrive at a complete understanding of this embodiment.

Electrode assembly 140 comprises three segmented electrodes 142 (only two electrodes 142 are visible in the perspective view of FIG. 2) spaced angularly around the longitudinal axis X-X. A structure 150 separates the segmented electrodes during manufacturing and assembly.

Structure 150 holds segmented electrodes 142 in an angular configuration. In the embodiment illustrated in FIG. 2, structure 150 comprises three strips 152, 154, and 156 of BIONATE® tape. Strip 152 is shown attached to segmented electrode 142. In some embodiments, middle portions of each strip 152, 154 and 156 are placed next to the inner tube and the adjoining side portions are folded and placed next to adjacent side portions of adjacent strips to form ribs 158, 160, and 162. The ribs 158, 160, and 162 act as angular spacers for the segmented electrodes 142.

In certain embodiments, the segmented electrodes 142 have a cross-sectional shape which is similar to a tube which has been flattened along a curved surface. For instance, the "top" segmented electrode 142 has a convex surface 164 which is sized to match the exterior surface of the lead body. In certain embodiments, the top segmented electrode 142 may also have a concave surface 166 designed to fit against the strip 152. The top segmented electrode 142 has a longitudinal aperture 168 which allows for one or more conductors to pass through.

In some embodiments, the segmented electrodes 142 may be formed by "flattening" a substantially annular ring of conductive material to produce the convex surface 164 and the concave surface 166. During the lead fabrication process, force is preferably applied to segmented electrodes 142 to crush or otherwise deform electrodes 142 about respective conductors. Upon deformation, the segmented electrode 142 locks the conductor in place. Further, the pressure contact between the segmented electrode 142 and the conductors causes a suitable electrical connection to be formed between the two components. In certain embodiments, the segmented electrode 142 may be additionally or alternatively welded to the conductor 170.

In certain embodiments, aperture 168 of the segmented electrodes, allows the body material to flow into the aperture during the overmolding process. Thus, the aperture 168 engages and anchors the segmented electrode 142 to the lead body after the overmolding process is completed.

In another embodiment, a respective elongated strip, rod, or ribbon of material (e.g., the same material used to implement electrodes 142) is placed through the aperture defined by each electrode 142. After deformation of electrode 142 to secure the conductor to the electrode 142, the strip or ribbon of material is bent to form an anchor that will be mechanically engaged by the insulative material after the overmolding is performed.

Figure 3A:
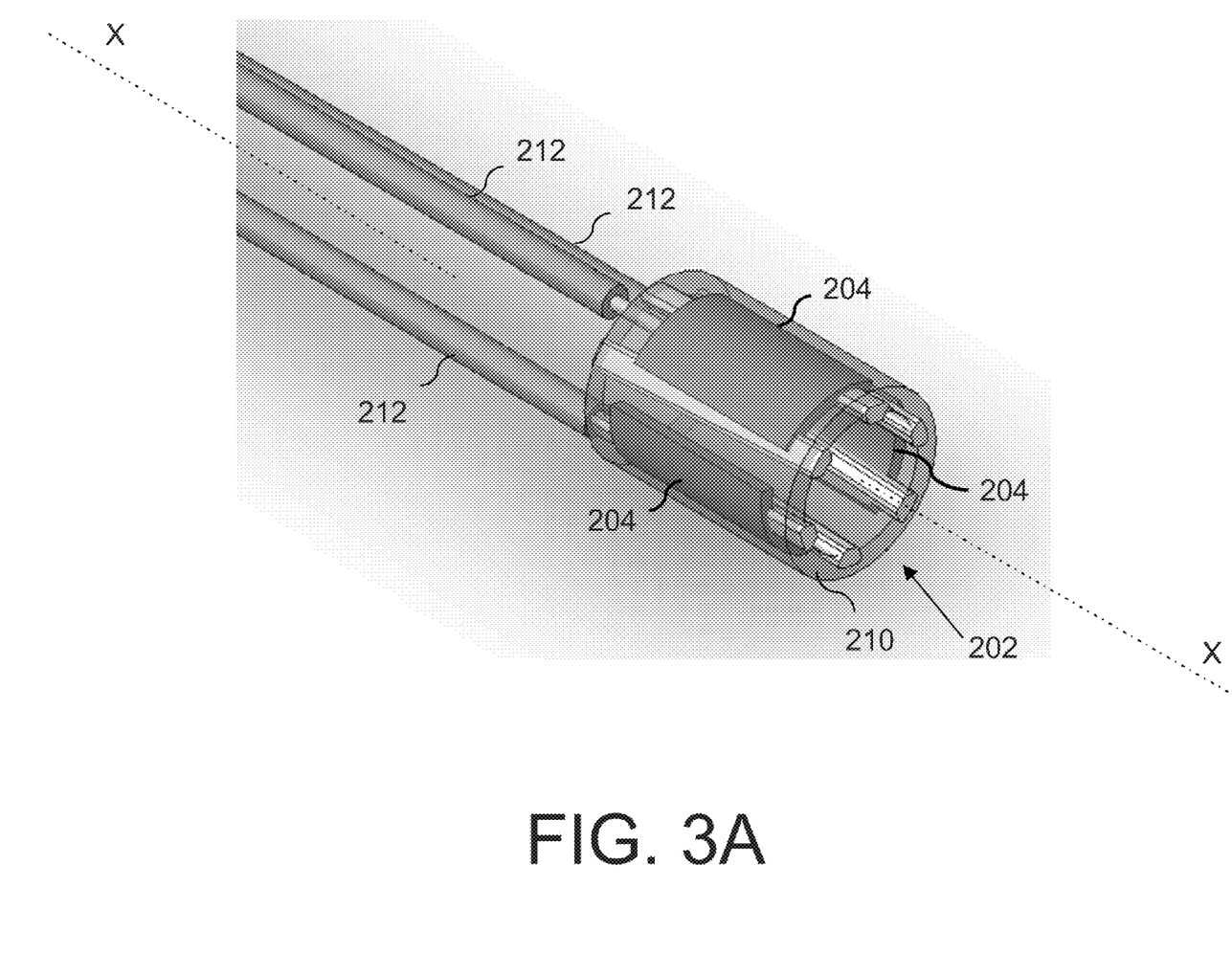
FIG. 3A is an isometric view of another inventive electrode assembly.

FIG. 3A depicts fabrication of array 202 of segmented electrodes according to another representative embodiment. Although only one array 202 is shown in FIG. 3A, multiple arrays 202 could be fabricated in series according to representative embodiments. The fabrication of a stimulation lead using one or more arrays 202 may occur in a similar manner to the fabrication processed discussed in regard to electrode assemblies 80 and 140. In FIG. 3A, the center tube and the spacers have been removed for clarity so the reader will focus on the electrode array 202. For brevity and clarity, a description of many components which are identical or similar to those described in connection with the above embodiments will not be repeated here. Reference should be made to the foregoing paragraphs with the following description to arrive at a complete understanding of this embodiment.

As illustrated, the electrode array 202 comprises three segmented electrodes 204 spaced angularly around the longitudinal axis X-X. In this embodiment, the segmented electrodes are encased in an encasement 210. Encasement 210 separates the segmented electrodes 204 during manufacturing and assembly angularly about the longitudinal axis X-X. The encasement 210 may be made of a flexible, biocompatible, thermoplastic material as described above in reference to other embodiments of the angular folds, and thus will fuse with other material of the lead body during an injection molding process as described above.

The segmented electrodes 204 may also be coupled to a plurality of wires 212 attached to or embedded in the encasement 210. The plurality of wires 212 are arranged angularly about the longitudinal axis X-X. In certain alternative embodiments, the plurality of wires 212 may also serve as segmented electrodes themselves—especially if a large number of segmented electrodes are required.

In some embodiments, the exterior face or exterior surface of each wire in the plurality of wires is increased to allow the wire to function as an electrode when positioned within the array 202. Increasing the exterior surface of each wire may be accomplished by burnishing the wire. As previously mentioned, if the burnishing creates sufficient surface area for a segmented electrode, molding may then be performed and a segment of burnished wire is exposed through the insulative material to form each segmented electrode. Alternatively, a respective thin sheet of a conducting material (e.g., the segmented electrode designs discussed above in regard to FIGS. 1A-1F and FIG. 2) is first attached to each wire to form the segmented electrode. Additionally, the thin sheet or segmented electrodes can be attached to more than one wire as illustrated in FIG. 3A.

Figure 3B:
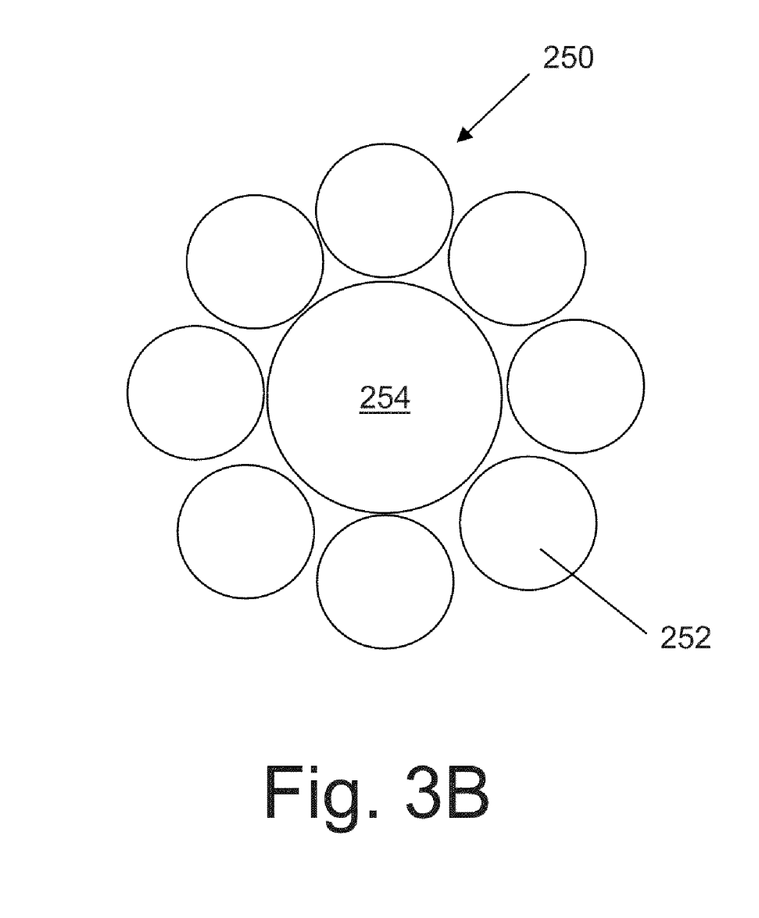
FIG. 3B is a cross-section of a twisted wire.
Figure 3C:
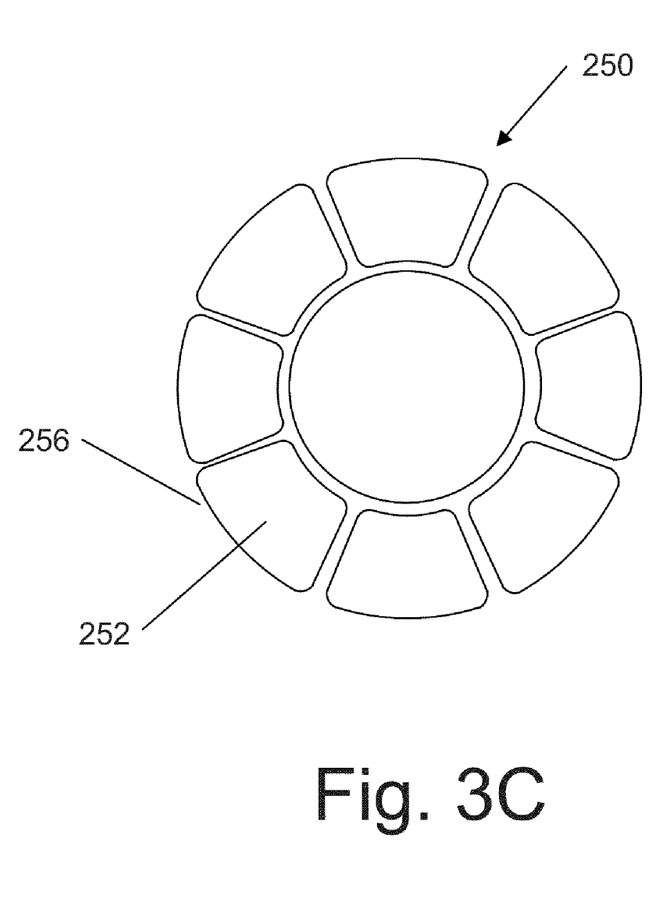
FIG. 3C is a cross-section of the twisted wire of FIG. 3B after burnishing.

The array 202 may be fabricated in a variety of processes. In one process, the array 202 may be made from a tightly stranded wire having a number of strands twisted around a core. A cross-section of such a wire 250 is illustrated in FIG. 3B. The number of individual strands 252 in the wire 250 is equal to the number of electrodes or wires ultimately desired in the array 202. In the illustrated embodiment, the strands 252 are twisted around a core 254. In alternative embodiments, the core 254 may not be necessary. The stranded wire 250 is processed through a burnishing machine which reshapes the individual strands 252. FIG. 3C represents a cross section of the wire 250 after it has been processed by a burnishing operation. As illustrated, the exterior surfaces 256 of the individual strands 252 have been flattened and enlarged by the burnishing operation.

The burnished wire 250 would then be untwisted in a controlled manner so that the strands 252 separate and expand from one another. The separated strands 252 may then be passed through an extruder (not shown). The extruder deposits a polymer, such as a thermoplastic urethane, in the interstitial spaces and over the outside of the strands. When the polymer solidifies, a wire encasement of trapezoidal shape strands encased in a polymer is formed. The wire encasement may then be cut to predetermined lengths and further processed. For instance, in one embodiment, a laser may cut a central bore through the wire encasement, creating the array 202. Additional lasers may ablate the polymer over the trapezoidal shape wires to expose their exterior surfaces. The exposed exterior surfaces may then be used to form stimulation electrodes or pads for attaching a thin sheet of conducting material as discussed above.

Figure 4:
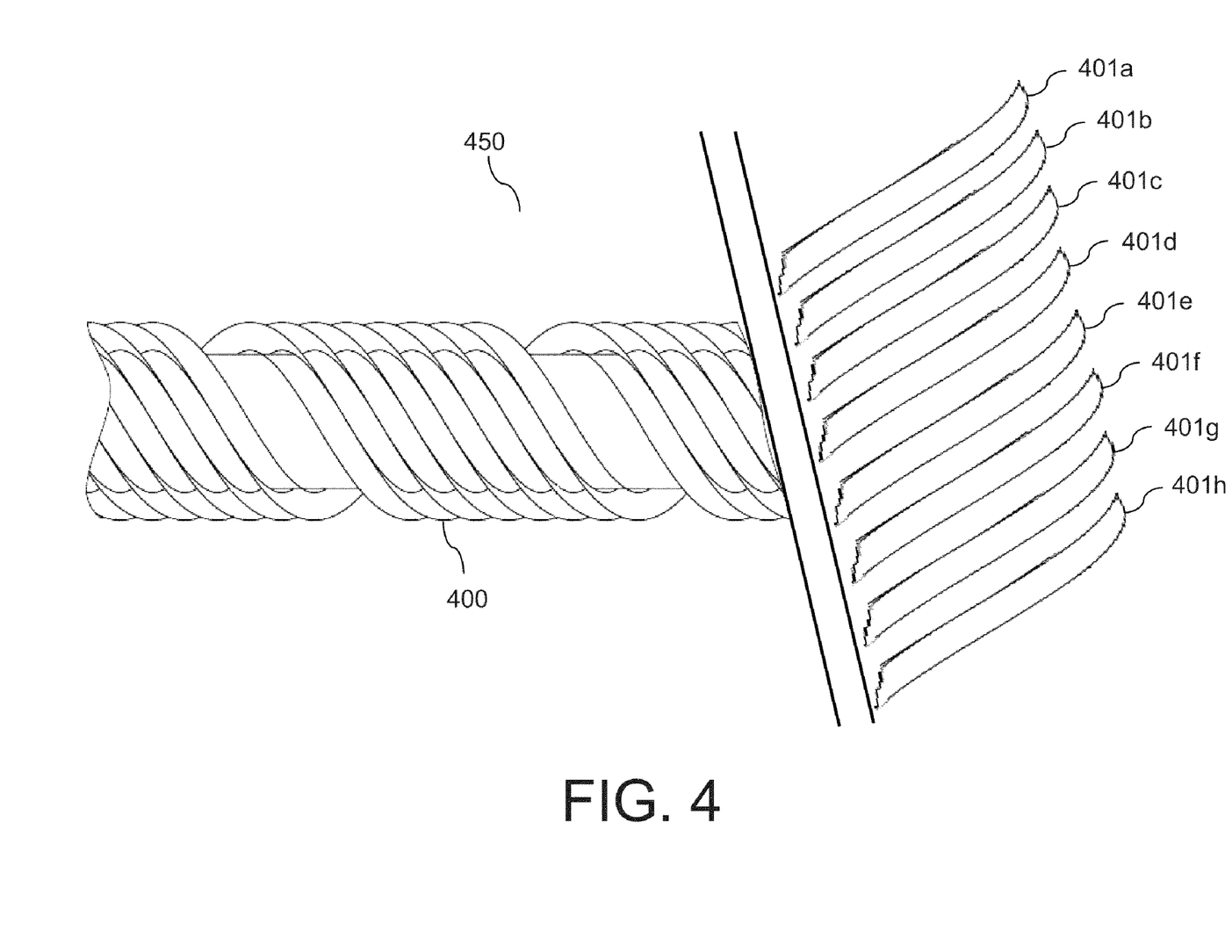
FIG. 4 illustrates a portion of a medical lead showing separated conductors.

FIG. 4 depicts intermediate lead assembly 450 adapted for connection to an array of segmented electrode assemblies. Lead assembly 450 comprises lead body 400 with a suitable number of conductors (shown individually as conductors 401a-401h) embedded or otherwise enclosed within insulative material. Conductors 401 are provided to conduct electrical pulses from the proximal end of lead assembly 450 to the distal end of lead assembly 450. Lead body 400 may be fabricated using any known or later developed processes. Examples of various lead body fabrication processes are disclosed in U.S. Pat. Nos. 6,216,045, 7,287,366, U.S. Patent Application Publication No. 20050027340A1, and U.S. Patent Application Publication No. 20070282411A1, which are incorporated herein by reference.

As is known in the art, each individual conductor 401 is commonly provided with a thin coating of a higher durometer insulator such as perfluoroalkoxyethylene (PFA). The purpose of the higher durometer coating is to ensure that the wire within the conductor 401 remains insulated in the event that the softer polymer material of the lead body 400 is breached or otherwise fails while the lead body 400 is implanted within a patient. The conductors 401 are commonly helically wound and insulative material (e.g., a polyurethane, PURSIL®, CARBOSIL®, etc.) is applied over the conductors to hold conductors 401 in place and to support conductors 401. Other common types of lead bodies provide individually coiled conductors within separate lumens of a lead body. Such lead bodies may also be utilized according to some embodiments.

As shown in FIG. 4, the insulative material of the lead body 400 is removed at the distal end of lead body 400 to permit access to a length of each conductor 401. For example, a suitable laser (e.g., a UV laser) can be used to remove the insulative material over a controlled portion of the pre-formed lead body 400 to release a length of each conductor 401 from lead body 400. Alternatively, manual stripping may be performed to release each conductor 401. Depending upon the type of harder insulative material applied to each individual conductor 401, a separate process may be used to further expose a portion of the wire of each conductor. At which point, intermediate lead assembly 450 may then be utilized in the processes discussed in regard to FIGS. 1A-1E, 2, and 3.

Figure 5:
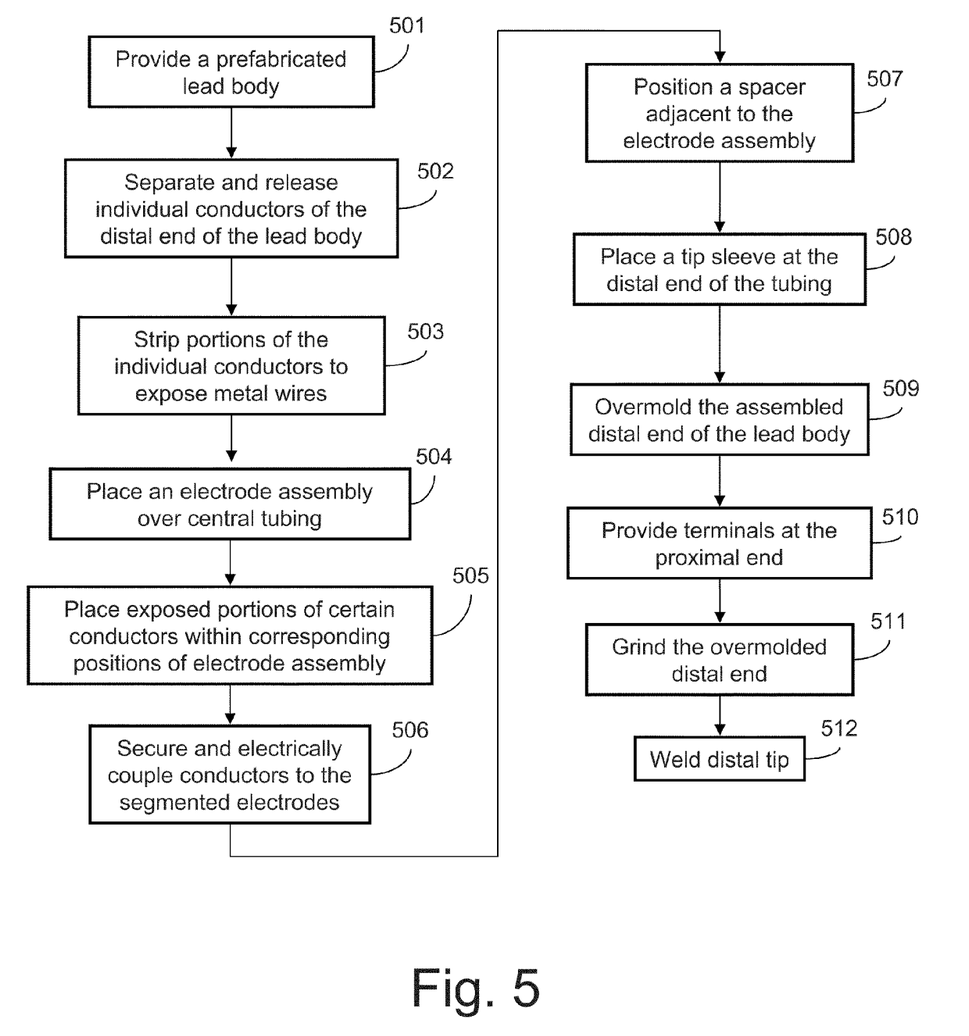
FIG. 5 depicts an inventive process of fabricating a medical lead that includes one or more segmented electrodes.

FIG. 5 depicts a process for fabricating a stimulation lead comprising segmented electrodes according to one representative embodiment. In 501, a pre-fabricated lead body is provided. In 502, a distal end of the lead body is processed to separate and release individual conductors from the distal end of the lead body. In 503, portions of the conductors are stripped to expose the metal wires.

In 504, an electrode assembly is placed over the center tubing of the lead body (and, possibly over a subset of conductors intended for one or more subsequent electrode assemblies). In 505, the exposed portions of a subset of conductors are placed within suitable positions defined in the electrode assembly. For example, the exposed portions of these conductors could be placed through the segmented electrodes 142 (shown in FIG. 2). Alternatively, the exposed portions of these conductors could be placed in indents 108 (shown in FIG. 1C). In 506, the conductors are secured and electrically coupled to the segmented electrodes (e.g., laser welding and/or crushing of the electrode about the conductor).

In 507, a spacer may be placed adjacent to the electrode assembly. Items 504-507 may be repeated a suitable number of times. In 508, a transition sleeve is placed at the distal end of the tubing. It shall be appreciated that ring electrodes can also be provided at any suitable position before, between, or after any group or groups of segmented electrodes.

In 509, the distal end of the lead body with the electrode assemblies, spacers, and transition sleeve are placed within a mold and overmolding is performed. During the overmolding step, the insulative material of the various components are placed in a state of flow, which, at least in part, results in a filling of regions between and underneath the respective components. Consequently, the electrodes are partially surrounded (i.e., along an interior surface) and supported by a fused matrix of material. As the insulative material of the spacers and support structures are formed of a material that possess substantially the same thermoplastic molding properties as the material of the lead body, the stimulation portion of the stimulation lead is stabilized and strengthened while also retaining its flexibility. In 510, terminals are provided to electrically couple to conductors of the lead body at the proximal end of the lead body to complete the stimulation lead.

In 511, centerless grinding is performed to remove excess material to cause the lead to possess a uniform outer. In 512, a hemispherical distal tip is preferably welded to the lead.

As discussed in regard to FIGS. 4 and 5, some representative embodiments obtain wire conductors for electrode assemblies from a pre-fabricated stimulation lead. Other embodiments may fabricate a stimulation lead by separately fabricating a lead body and a stimulation end including segmented electrode assemblies. After fabrication of the two components separately, conductors of the two separate components can be "spliced" together to form the finalized stimulation lead.

Figure 6A:
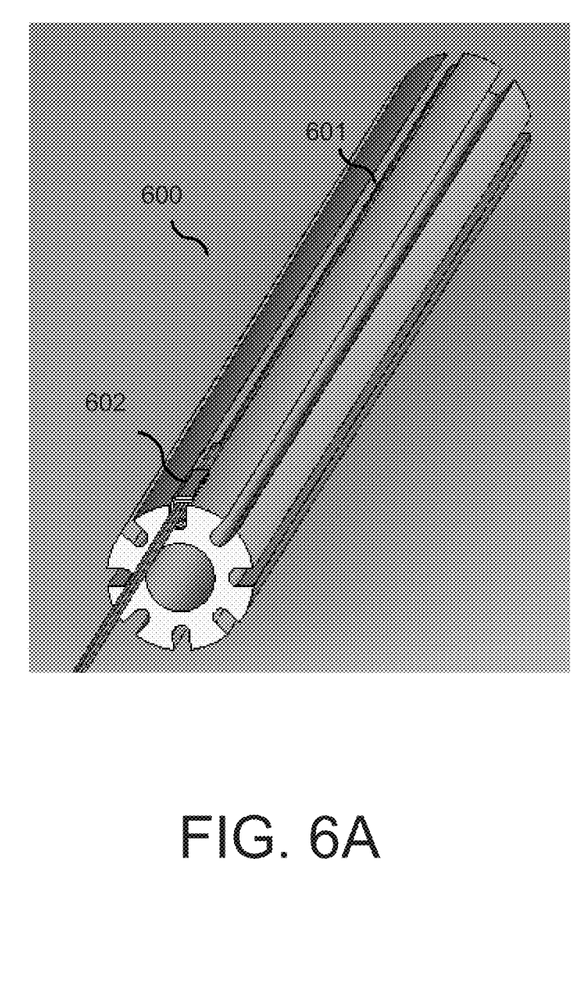
FIG. 6A is a isometric view of an inventive splicing tube for use in fabrication of stimulation leads.
Figure 6B:
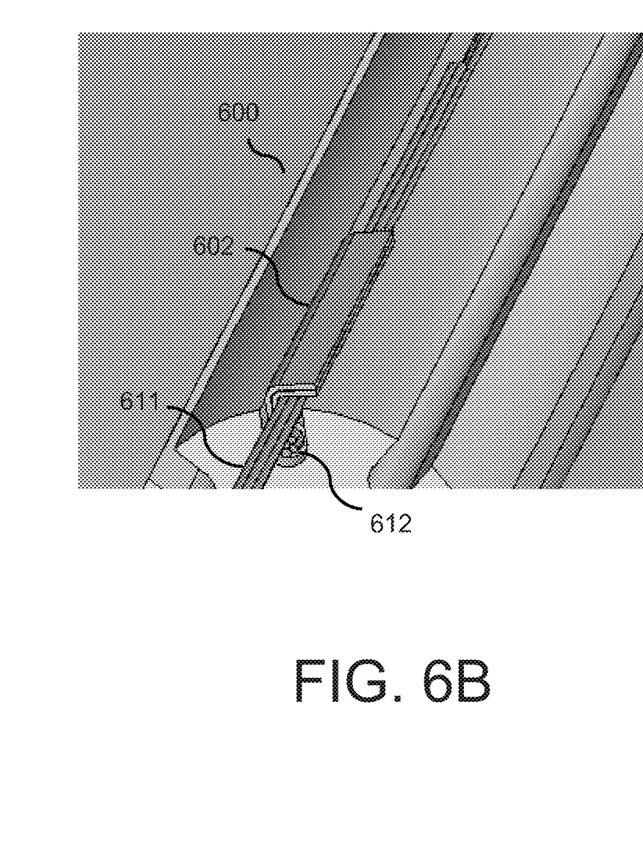
FIG. 6B is a detailed view of FIG. 6A.

FIGS. 6A and 6B depict splicing tube 600 for facilitating splicing of conductors wires during fabrication of a stimulation lead. FIG. 6A depicts a full view of tube 600 and FIG. 6B depicts a detailed view of tube 600 to show conductor detail. Although splicing tube 600 is advantageous for coupling an array of segmented electrodes to a pre-formed lead body, splicing tube 600 is not limited to such applications. For example, splicing tube 600 could also be utilized to facilitate coupling between the paddle of a lamitrode type stimulation lead to a lead body.

In one embodiment, separate conductor wires are cut to length and provided for connection to segmented electrodes assemblies (such as those discussed in regard to FIGS. 1A-1E and FIG. 2). Center tubing is provided about a mandrel and electrode assemblies are inserted over the tubing with spacers preferably interspersed between the assemblies. Respective conductors are coupled to the various segmented electrodes during the assembly process. Tip electrodes and or ring electrodes may also be provided over the tubing and coupled to respective conductors.

At this point, a lead body is processed to release individual conductors from a distal end of the lead body (see FIG. 4). The released ends of respective conductors from the lead body are placed within grooves of splicing tube 600 (e.g., conductor 612 is shown placed within groove 601 as shown in FIGS. 6A and 6B). The proximal ends of the wires from the array of electrode assemblies are also placed within the grooves of splicing tube 600 (e.g., conductor 611 is shown placed over conductor 612 in FIG. 6B).

Conductive filler material 602 is preferably provided for each pair of conductors in the grooves of splicing tube 600. In one embodiment, material 602 is provided in ribbon form about each pair of conductors. Material 602 and the pair of conductors are subjected to laser welding. The welding preferably causes material 602 to flow into the strands of the conductor wires making both a mechanical and electrical connection.

The lead body, the splicing tube, and the electrode array are subjected to overmolding. In one preferred embodiment, the splicing tube is formed of thermoplastic material that flows and fuses with the overmolding material, the material of the lead body, the material of the electrode assembly, etc. Accordingly, upon overmolding, an integrated stimulation lead is formed that is substantially free of gaps and free of weakened transitions between separate non-fused layers of insulative material. Finally, suitable grinding techniques are applied to provide a uniform diameter along the lead.

Figure 7A:
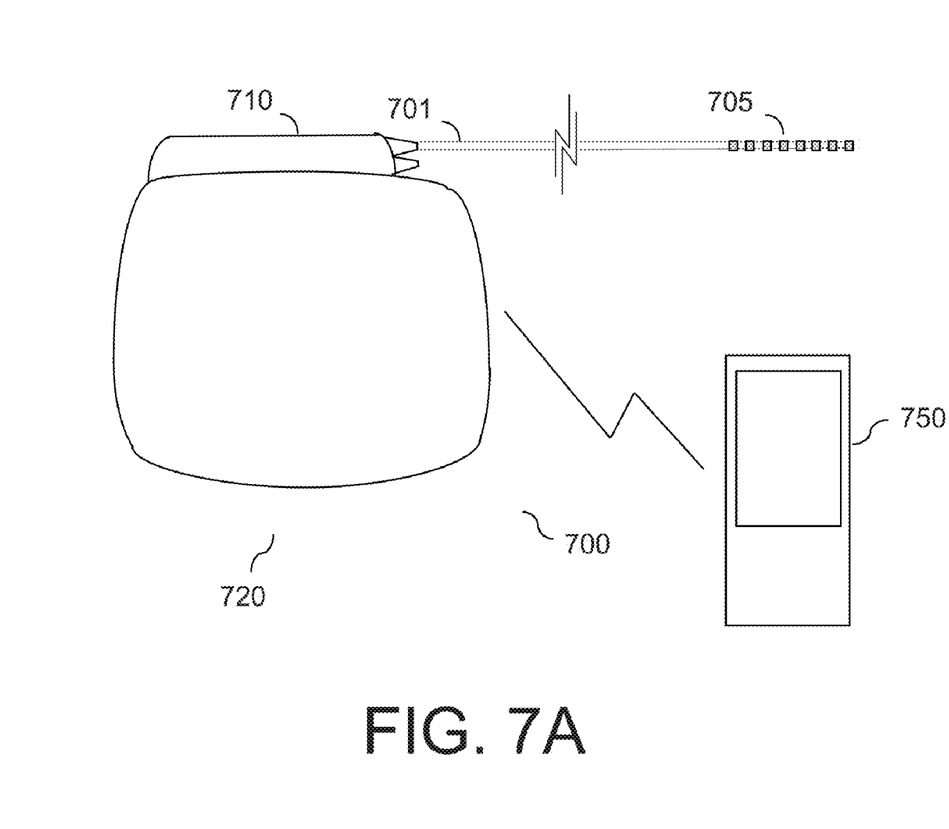
FIG. 7A depicts an inventive stimulation system that includes segmented electrodes.

FIG. 7A depicts stimulation system 700 according to one representative embodiment. Neurostimulation system 700 includes pulse generator 720 and one or more stimulation leads 701. Examples of commercially available pulse generator include the EON®, EON MINI®, and the LIBRA® pulse generators available from St. Jude Medical Neuromodulation Division. Pulse generator 720 is typically implemented using a metallic housing that encloses circuitry for generating the electrical pulses for application to neural tissue of the patient. Control circuitry, communication circuitry, and a rechargeable battery (not shown) are also typically included within pulse generator 720. Pulse generator 720 is usually implanted within a subcutaneous pocket created under the skin by a physician.

Lead 701 is electrically coupled to the circuitry within pulse generator 720 using header 710. Lead 701 includes terminals (not shown) that are adapted to electrically connect with electrical connectors (e.g., "Bal-Seal" connectors which are commercially available and widely known) disposed within header 710. The terminals are electrically coupled to conductors (not shown) within the lead body of lead 701. The conductors conduct pulses from the proximal end to the distal end of lead 701. The conductors are also electrically coupled to electrodes 705 to apply the pulses to tissue of the patient. Lead 701 can be utilized for any suitable stimulation therapy. For example, the distal end of lead 701 may be implanted within a deep brain location or a cortical location for stimulation of brain tissue. The distal end of lead 701 may be implanted in a subcutaneous location for stimulation of a peripheral nerve or peripheral nerve fibers. Alternatively, the distal end of lead 701 positioned within the epidural space of a patient. Although some embodiments are adapted for stimulation of neural tissue of the patient, other embodiments may stimulate any suitable tissue of a patient (such as cardiac tissue). An "extension" lead (not shown) may be utilized as an intermediate connector if deemed appropriate by the physician.

Figure 7B:
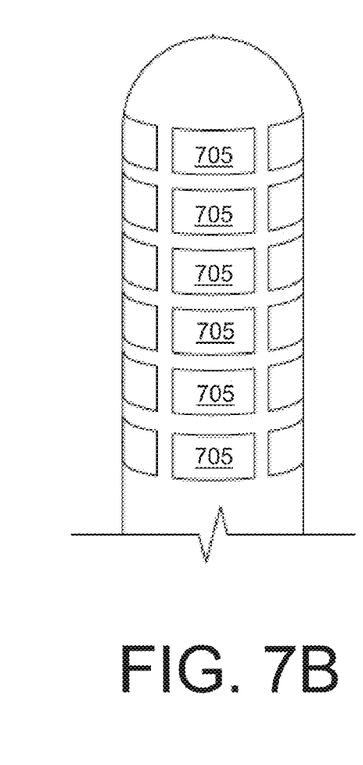
FIG. 7B is a detailed view of medical lead which may be used with the system of FIG. 7A.

Electrodes 705 include multiple segmented electrodes as shown in FIG. 7B. The use of segmented electrodes permits the clinician to more precisely control the electrical field generated by the stimulation pulses and, hence, to more precisely control the stimulation effect in surrounding tissue. Electrodes 705 may also include one or more ring electrodes or a tip electrode. Any of the electrode assemblies and segmented electrodes discussed herein can be used for the fabrication of electrodes 705. Electrodes 705 may be utilized to electrically stimulate any suitable tissue within the body including, but not limited to, brain tissue, tissue of the spinal cord, peripheral nerves or peripheral nerve fibers, digestive tissue, cardiac tissue, etc. Electrodes 705 may also be additionally or alternatively utilized to sense electrical potentials in any suitable tissue within a patient's body.

Pulse generator 720 preferably wirelessly communicates with programmer device 750. Programmer device 750 enables a clinician to control the pulse generating operations of pulse generator 720. The clinician can select electrode combinations, pulse amplitude, pulse width, frequency parameters, and/or the like using the user interface of programmer device 750. The parameters can be defined in terms of "stim sets," "stimulation programs," (which are known in the art) or any other suitable format. Programmer device 750 responds by communicating the parameters to pulse generator 720 and pulse generator 720 modifies its operations to generate stimulation pulses according to the communicated parameters.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

What is claimed is:

1. A process for fabricating a medical lead for stimulation of tissue of a patient, the process comprising:
   providing an electrode assembly comprising a plurality of electrodes electrically coupled to a first plurality of conductors;
   providing a lead body comprising a second plurality of conductors;
   providing a splicing tube having a plurality of angularly spaced longitudinal grooves;
   placing proximal ends of the first plurality of conductors within the plurality of angularly spaced grooves defined on an exterior surface of the splicing tube;
   placing distal ends of the second plurality of conductors within the plurality of angularly spaced grooves and adjacent to the proximal ends of the first plurality of conductors such that a portion of the distal ends overlap a portion of the proximal ends;
   positioning conductive filler material adjacent to the overlapped portions of the distal and proximal ends;
   electrically coupling the proximal ends of the first plurality of electrodes to respective distal ends of the second plurality of electrodes;
   molding insulative material about at least the electrode assembly and the splicing tube; and
   fusing the splicing tube with the insulative material from the molding and the lead body.

2. The process of claim 1, wherein the electrically coupling comprises laser welding the conductive filler material such that the conductive filler material couples the proximal ends of the first plurality of conductors to respective distal ends of the second plurality of conductors.

3. The process of claim 1, further comprising:
   removing insulative material of the lead body to release the second plurality of conductors.

4. The process of claim 1, further comprising:
   providing a center tubing about a mandrel;
   positioning the electrode assembly over the center tubing; and
   positioning at least one spacer adjacent to the at least one electrode assembly; and
   providing a second electrode assembly adjacent to the at least one spacer.

5. The process of claim 4, further comprising:
   positioning a ring electrode over the center tubing; and
   positioning a spacer adjacent to the ring electrode.

6. The process of claim 1, further comprising performing centerless grinding after performing the molding.

7. The process of claim 1 wherein the plurality of electrodes of the electrode assembly are segmented electrodes.

8. The process of claim 7 further comprising:
   attaching the segmented electrodes about a central tubing.

9. The process of claim 8 further comprising:
   maintaining angular separation between the segmented electrodes using thermoplastic tape.

10. The process of claim 7 wherein the segmented electrodes have a cross-section being generally crescent shaped.

11. The process of claim 10 further comprising:
    crushing each segmented electrode about a respective conductor of the first plurality of conductors.

12. A process for fabricating a medical lead for stimulation of tissue of a patient, the process comprising:
    providing an electrode assembly comprising a plurality of segmented electrodes electrically coupled to a first plurality of conductors;
    providing a lead body comprising a second plurality of conductors;
    providing a splicing tube having a plurality of angularly spaced longitudinal grooves;
    placing proximal ends of the first plurality of conductors within the plurality of angularly spaced grooves defined on an exterior surface of the splicing tube;
    placing distal ends of the second plurality of conductors within the plurality of angularly spaced grooves and adjacent to the proximal ends of the first plurality of conductors such that a portion of the distal ends overlap a portion of the proximal ends;
    positioning conductive filler material adjacent to the overlapped portions of the distal and proximal ends;
    electrically coupling the proximal ends of the first plurality of electrodes to respective distal ends of the second plurality of electrodes;
    molding insulative material about at least the electrode assembly and the splicing tube; and
    fusing the splicing tube with the insulative material from the molding and the lead body.

13. The process of claim 12, wherein the electrically coupling comprises laser welding the conductive filler material such that the conductive filler material couples the proximal ends of the first plurality of conductors to respective distal ends of the second plurality of conductors.

14. The process of claim 12, further comprising:
    removing insulative material of the lead body to release the second plurality of conductors.

15. The process of claim 12, further comprising:
    providing a center tubing about a mandrel;
    positioning the electrode assembly over the center tubing; and
    positioning at least one spacer adjacent to the at least one electrode assembly; and
    providing a second electrode assembly adjacent to the at least one spacer.

16. The process of claim 15, further comprising:
    positioning a ring electrode over the center tubing; and
    positioning a spacer adjacent to the ring electrode.

17. The process of claim 12, further comprising performing centerless grinding after performing the molding.

18. The process of claim 12 further comprising:
    attaching the segmented electrodes about a central tubing.

19. The process of claim 18 further comprising:
    maintaining angular separation between the segmented electrodes using thermoplastic tape.

* * * * *